United States Patent
Black et al.

(10) Patent No.: US 7,928,091 B2
(45) Date of Patent: Apr. 19, 2011

(54) CATHEPSIN CYSTEINE PROTEASE INHIBITORS

(75) Inventors: Cameron Black, Baie d'Urfe (CA); Sheldon Crane, Pierrefonds (CA); Renata Oballa, Kirkland (CA); Joel Robichaud, Dollard des Ormeaux (CA)

(73) Assignee: Merck Frosst Canada Ltd., Quebec (CA)

( * ) Notice: Subject to any disclaimer, the term of this patent is extended or adjusted under 35 U.S.C. 154(b) by 506 days.

(21) Appl. No.: 11/988,346

(22) PCT Filed: Jul. 5, 2006

(86) PCT No.: PCT/CA2006/001104
§ 371 (c)(1),
(2), (4) Date: Jan. 3, 2008

(87) PCT Pub. No.: WO2007/003056
PCT Pub. Date: Jan. 11, 2007

(65) Prior Publication Data
US 2009/0093444 A1 Apr. 9, 2009

Related U.S. Application Data

(60) Provisional application No. 60/696,970, filed on Jul. 6, 2005.

(51) Int. Cl.
*A61K 31/663* (2006.01)
*C07D 231/12* (2006.01)

(52) U.S. Cl. ...... 514/108; 514/167; 514/406; 548/377.1

(58) Field of Classification Search ................ None
See application file for complete search history.

(56) References Cited

FOREIGN PATENT DOCUMENTS

| | | |
|---|---|---|
| CA | 2410303 | 12/2001 |
| CA | 2466115 | 5/2003 |
| CA | 2527632 | 12/2004 |
| CA | 2530068 | 1/2005 |
| WO | WO0149288 | 7/2001 |

*Primary Examiner* — Kamal A Saeed
(74) *Attorney, Agent, or Firm* — Nicole M. Beeler; David A. Muthard

(57) ABSTRACT

This invention relates to a novel class of compounds which are cysteine protease inhibitors, including but not limited to, inhibitors of cathepsins K, L, S and B. These compounds are useful for treating diseases in which inhibition of bone resorption is indicated, such as osteoporosis.

9 Claims, No Drawings

CATHEPSIN CYSTEINE PROTEASE INHIBITORS

PRIORITY CLAIM

This application is a §371 National Stage Application of PCT/CA2006/001104 filed on Jul. 05, 2006, which claims priority from U.S. Provisional Application Ser. No. 60/696,970, filed on Jul. 06, 2005.

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, hypercalcemia of malignancy or multiple myeloma. One of the most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Cathepsins belong to the papain superfamily of cysteine proteases. These proteases function in the normal physiological as well as pathological degradation of connective tissue. Cathepsins play a major role in intracellular protein degradation and turnover and remodeling. To date, a number of cathepsin have been identified and sequenced from a number of sources. These cathepsins are naturally found in a wide variety of tissues. For example, cathepsin B, C, F, H, L, K, O, S, V, W, and Z have been cloned. Cathepsin L is implicated in normal lysosomal proteolysis as well as several diseases states, including, but not limited to, metastasis of melanomas. Cathepsin S is implicated in Alzheimer's disease, atherosclerosis, chronic obstructive pulmonary disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. Increased Cathepsin B levels and redistribution of the enzyme are found in tumors, suggesting a role in tumor invasion and metastasis. In addition, aberrant Cathepsin B activity is implicated in such disease states as rheumatoid arthritis, osteoarthritis, pneumocystisis carinii, acute pancreatitis, inflammatory airway disease and bone and joint disorders.

Mammalian cathepsins are related to the papain-like cysteine proteases expressed by disease-causing parasites including those from the families protozoa, platyhelminthes, nematodes and arthropodes. These cysteine proteases play an essential role in the life cycle of these organisms.

Human type I collagen, the major collagen in bone is a good substrate for cathepsin K. See Kafienah, W., et al, 1998, *Biochem J* 331:727-732, which is hereby incorporated by reference in its entirety. In vitro experiments using antisense oligonucleotides to cathepsin K, have shown diminished bone resorption in vitro, which is probably due to a reduction in translation of cathepsin K mRNA. See Inui, T., et al, 1997, *J Biol Chem* 272:8109-8112, which is hereby incorporated by reference in its entirety. The crystal structure of cathepsin K has been resolved. See McGrath, M. E., et al., 1997, *Nat Struct Biol* 4:105-109; Zhao, B., et al, 1997, *Nat Struct Biol* 4:109-11, which are hereby incorporated by reference in their entirety. Also, selective peptide based inhibitors of cathepsin K have been developed See Bromme, D., et al, 1996, *Biochem J* 315:85-89; Thompson, S. K., et al, 1997, *Proc Natl Acad Sci USA* 94:14249-14254, which are hereby incorporated by reference in their entirety. Accordingly, inhibitors of Cathepsin K can reduce bone resorption. Such inhibitors would be useful in treating disorders involving bone resorption, such as osteoporosis.

What is needed in the art are therapeutic agents to treat diseases associated with Cathepsin K activity including osteoporosis, glucocorticoid induced osteoporosis, Paget's disease, abnormally disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease and cancer including metastatic bone disease, hypercalcemia of malignancy, and multiple myeloma.

SUMMARY OF THE INVENTION

The present invention relates to compounds that are capable of treating and/or preventing cathepsin dependent conditions or disease states in a mammal in need thereof. One embodiment of the present invention is illustrated by a compound of Formula I, and the pharmaceutically acceptable salts, stereoisomers and N-oxide derivatives thereof:

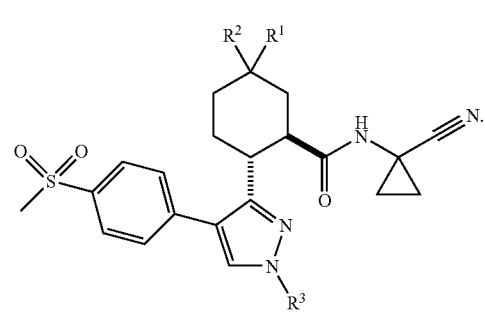

DETAILED DESCRIPTION OF THE INVENTION

The present invention relates to compounds of the following chemical formula:

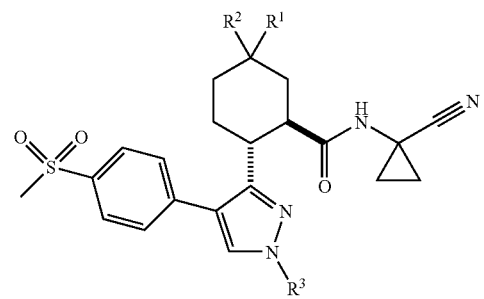

wherein $R^1$ is halo;

$R^2$ is halo;

$R^3$ is hydrogen, $C_{1-6}$ alkyl, $C_{1-6}$ haloalkyl, $C_{3-6}$ cycloalkyl, aryl or heteroaryl;

or a pharmaceutically acceptable salt, stereoisomer or N-oxide derivative thereof.

In an embodiment of the invention, or $R^1$ is fluoro or chloro.

In an embodiment of the invention, or $R^2$ is fluoro or chloro.

In an embodiment of the invention, $R^3$ is hydrogen, $C_{1-6}$ alkyl or $C_{1-6}$ haloalkyl. In a class of the invention, $R^3$ is $C_{1-6}$ haloalkyl. In a subclass of the invention, $R^3$ is 2,2,2-trifluoroethyl.

Reference to the preferred embodiments set forth above is meant to include all combinations of particular and preferred groups unless stated otherwise.

Specific embodiments of the present invention include, but are not limited to:

(1R,2R)-N-(1-cyanocyclopropyl)-5,5-difluoro-2-[4-[4-(methylsulfonyl)phenyl]-1H-pyrazol-3-yl]cyclohexanecarboxamide;

(1R,2R)-N-(1-cyanocyclopropyl)-5,5-difluoro-2-[4-[4-(methylsulfonyl)phenyl]-1-methyl-1H-pyrazol-3-yl]cyclohexanecarboxamide;

(1R,2R)-N-(1-cyanocyclopropyl)-5,5-dichloro-2-[4-[4-(methylsulfonyl)phenyl]-1-methyl-1H-pyrazol-3-yl]cyclohexanecarboxamide;

(1R,2R)-N-(1-cyanocyclopropyl)-5,5-difluoro-2-[4-[4-(methylsulfonyl)phenyl]-1-(2,2,2-trifluoroethyl)-1H-pyrazol-3-yl]cyclohexanecarboxamide;

(1R,2R)-N-(1-cyanocyclopropyl)-5,5-dichloro-2-[4-[4-(methylsulfonyl)phenyl]-1-(2,2,2-trifluoroethyl)-1H-pyrazol-3-yl]cyclohexanecarboxamide;

or a pharmaceutically acceptable salt, stereoisomer or N-oxide derivative thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

Utilities

The compounds of the present invention are inhibitors of cathepsins and are therefore useful to treat or prevent cathepsin dependent diseases or conditions in mammals, preferably humans. Specifically, the compounds of the present invention are inhibitors of Cathepsin K and are therefore useful to treat or prevent Cathepsin K dependent diseases or conditions in mammals, preferably humans.

The compounds of the present invention have advantages over structurally similar compounds known in the art in that they have a marked improved metabolic and pharmacokinetic profiles. Specifically, the compounds of the instant invention have excellent bioavailability, as exemplified, but not limited to, a dose of 10 milligrams per kilogram in male Sprague Dawley rats in 0.5-1% methocel or PEG-200. Additionally, the compounds of the instant invention have improved half-lives in a number of preclinical animal species and, as a result, provide greater systemic drug exposure than structurally similar compounds known in the art.

"Cathepsin dependent diseases or conditions" refers to pathologic conditions that depend on the activity of one or more cathepsins. "Cathepsin K dependent diseases or conditions" refers to pathologic conditions that depend on the activity of Cathepsin K. Diseases associated with Cathepsin K activities include osteoporosis, glucocorticoid induced osteoporosis, Paget's disease, abnormally disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease and cancer including metastatic bone disease, hypercalcemia of malignancy, and multiple myeloma. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

An embodiment of the invention is a method of inhibiting cathepsin activity in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of treating or preventing cathepsin dependent conditions in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of inhibiting bone loss in a mammal in need thereof, comprising administering to the mammal a therapeutically effective amount of any of the compounds or any of the pharmaceutical compositions described above. Another embodiment of the invention is a method of reducing bone loss in a mammal in need thereof, comprising administering to the mammal a therapeutically effective amount of any of the compounds or any of the pharmaceutical compositions described above. The utility of cathepsin K inhibitors in the inhibition of bone resorption, which includes abnormally increased bone turnover, bone fractures, Paget's disease, osteogenesis imperfecta and periprosthetic osteolysis, is known in the literature, see Stroup, G. B., Lark, M. W., Veber, D F, Bhattacharrya, A., Blake, S., Dare, L. C., Erhard, K. F., Hoffman, S. J., James, I. E., Marquis, R. w., Ru, Y., Vasko-Moser, J. A., Smith, B. R., Tomaszek, T. and Gowen, M. Potent and selective inhibition of human cathepsin K leads to inhibition of bone resorption in vivo in a nonhuman primate. J. Bone Miner. Res., 16:1739-1746; 2001; and Votta, B. J., Levy, M. A., Badger, A., Dodds, R. A., James, I. E., Thompson, S., Bossard, M. J., Carr, T., Connor, J. R., Tomaszek, T. A., Szewczuk, L. Drake, F. H., Veber, D., and Gowen, M. Peptide aldehyde inhibitors of cathepsin K inhibit bone resorption both in vivo and in vitro. J. Bone Miner. Res. 12:1396-1406; 1997.

Another embodiment of the invention is a method of treating or preventing osteoporosis, including glucocorticoid induced osteoporosis, in a mammal in need thereof, comprising administering to the mammal a therapeutically effective amount of any of the compounds or any of the above pharmaceutical compositions described above. The utility of cathepsin K inhibitors in the treatment or prevention of osteoporosis is known in the literature, see Saftig, P., Hunziker, E., Wehmeyer, O., Jones, S., Boyde, A., Rommerskirch, W., Moritz, J. D., Schu, P., and Vonfigura, K. Impaired osteoclast bone resorption leads to osteopetrosis in cathepsin K-deficient mice. Proc. Natl. Acad. Sci. USA 95:13453-13458; 1998.

Another embodiment of the invention is a method of treating or preventing periodontal disease, including tooth loss, in a mammal in need thereof, comprising administering to the mammal a therapeutically effective amount of any of the compounds or any of the above pharmaceutical compositions described above. The utility of cathepsin K inhibitors in the treatment or prevention of periodontal disease and tooth loss is known in the literature, see Tsuji Y, et al., Expression of cathepsin K mRNA and protein in odontoclasts after experimental tooth movement in the mouse maxilla by in situ hybridization and immunoelectron microscopy. Cell Tissue Res. 2001 March; 303(3):359-69.

Another embodiment of the invention is a method of treating or preventing rheumatoid arthritic condition in a mammal in need thereof, comprising administering to the mammal a therapeutically effective amount of any of the compounds or any of the pharmaceutical compositions described above. It is known in the literature that progressive destruction of the periarticular bone is a major cause of joint dysfunction and disability in patients with rheumatoid arthritis (RA), see Goldring S R, "Pathogenesis of bone erosions in rheumatoid arthritis". Curr. Opin. Rheumatol. 2002; 14: 406-10. Analysis of joint tissues from patients with RA have provided evidence that cathepsin K positive osteoclasts are the cell types that mediate the focal bone resorption associated with rheumatoid synovial lesion, see Hou, W-S, Li, W, Keyszer, G, Weber, E, Levy, R, Klein, M J, Gravallese, E M, Goldring, S R. Bromme, D, "Comparison of Cathepsin K and S expression within the Rheumatoid and Osteoarthritic Synovium", Arthritis Rheumatism 2002; 46: 663-74. In addition, generalized bone loss is a major cause of morbidity associated with severe RA. The frequency of hip and spinal fractures is substantially increased in patients with chronic RA, see Gould A, Sambrook, P, Devlin J et al, "Osteoclastic activation is the principal mechanism leading to secondary osteoporosis in rheumatoid arthritis". J. Rheumatol. 1998; 25: 1282-9. The utility of cathepsin K inhibitors in the treatment or prevention of resorption in subarticular bone and of generalized bone loss represent a rational approach for pharmacological intervention on the progression of rheumatoid arthritis.

Another embodiment of the invention is a method of treating or preventing the progression of osteoarthritis in a mammal in need thereof, comprising administering to the mammal a therapeutically effective amount of any of the compounds or any of the pharmaceutical compositions described above. It is known in the literature that osteoarthritis (OA) is accompanied with well-defined changes in the joints, including erosion of the articular cartilage surface, peri-articular endochondral ossification/osteophytosis, and subchondral bony sclerosis and cyst formation, see Oettmeier R, Abendroth, K, "Osteoarthritis and bone: osteologic types of osteoarthritis of the hip", Skeletal Radiol. 1989; 18: 165-74. Recently, the potential contribution of subchondral bone sclerosis to the initiation and progression of OA have been suggested. Stiffened subchondral bone as the joint responding to repetitive impulsive loading, is less able to attenuate and distribute forces through the joint, subjecting it to greater mechanical stress across the articular cartilage surface. This in turn accelerates cartilage wear and fibrillate, see Radin, E L and Rose R M, "Role of subchondral bone in the initiation and progression of cartilage damage", Clin. Orthop. 1986; 213: 34-40. Inhibition of excessive subarticular bone resorption by an anti-resorptive agent such as a cathepsin K inhibitor, will lead to inhibition of subchondral bone turnover, thus may have a favorable impact on OA progression.

In addition to the above hypothesis, cathepsin K protein expression was recently identified in synovial fibroblasts, macrophage-like cells, and chondrocytes from synovium and articular cartilage specimens derived from OA patients, see Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74; and Dodd, R A, Connor, J R. Drake, F H, Gowen, M, "Expression of Cathepsin K messenger RNA in giant cells and their precursors in human osteoarthritic synovial tissues". Arthritis Rheumatism 1999; 42: 1588-93; and Konttinen, Y T, Mandelin, J, Li, T-F, Salo, J, Lassus, J et al. "Acidic cysteine endoproteinase cathepsin K in the degeneration of the superficial articular hyaline cartilage in osteoarthritis", Arthritis Rheumatism 2002; 46: 953-60. These recent studies thus implicated the role of cathepsin K in the destruction of collagen type II in the articular cartilage associated with the progression of osteoarthritis. The utility of cathepsin K inhibitors in the treatment or prevention of osteoarthritis as described in this invention thus comprise of two different mechanisms, one is on the inhibition of osteoclast-driven subchondral bone turnover, and two is on the direct inhibition of collagen type n degeneration in the synovium and cartilage of patients with OA.

Another embodiment of the invention is a method of treating cancer in a mammal in need thereof, comprising administering to the mammal a therapeutically effective amount of any of the compounds or any of the pharmaceutical compositions described above. It is known in the literature that cathepsin K is expressed in human breast carcinoma, prostate cancer and chordoma and has matrix degrading capabilities, see Littlewood-Evans A J, Bilbe G, Bowler W B, Farley D, Wlodarski B, Kokubo T, Inaoka T, Sloane J, Evans D B, Gallagher J A, "The osteoclast-associated protease cathepsin K is expressed in human breast carcinoma." Cancer Res 1997 Dec. 1; 57(23):5386-90, Brubaker K D, Vessella R L, True L D, Thomas R, Corey E "Cathepsin K mRNA and protein expression in prostate cancer progression." J Bone Miner Res 2003 18, 222-30, Haeckel C, Krueger S, Kuester D, Ostertag H, Samii M, Buehling F, Broemme D, Czerniak B, Roessner A. "Expression of cathepsin K in chordoma." Hum Pathol 2000 July; 31(7):834-40.

Another embodiment of the invention is a method of treating atherosclerosis in a mammal in need thereof, comprising administering to the mammal a therapeutically effective amount of any of the compounds or any of the pharmaceutical compositions described above. It is known in the literature that cathepsin K is expressed in human atheroma and has significant elastase activity, see Sukhova G K, Shi G P, Simon D I, Chapman H A, Libby P. "Expression of the elastolytic cathepsins S and K in human atheroma and regulation of their production in smooth muscle cells." J Clin Invest 1998 August 102, 576-83. It is also known that the Cat K null mouse when crossed with an ApoE null mouse shows reduced atherosclerotic plaque area and increased resistance to plaque rupture, see E. Lutgens, S. P. M. Lutgens, B. C. G. Faber, S. Heeneman, M. M. J. Gijbels, M. P. J. de Winther, P. Frederik, I. van der Made, D. Black, M. J. A. P. Daemen, K. B. J. M. Cleutjens "Disruption of the Cathepsin K Gene Reduces Atherosclerosis Progression and Induces Plaque Fibrosis but Accelerates Macrophage Foam Cell Formation." Circulation 2006 113: 98-107. Increased plaque stability would lead to a decrease in heart attack and stroke in a patient administered a therapeutically effective amound of any of the compounds or any of the pharmaceutical compositions described above.

Another embodiment of the invention is a method of treating obesity in a mammal in need thereof, comprising administering to the mammal a therapeutically effective amount of any of the compounds or any of the pharmaceutical compositions described above. It is known in the literature that cathepsin K mRNA is increased in adipose tissue in several mouse models of obesity and also in adipose tissue of obese human males, see Chiellini C, Costa M, Novelli S E, Amri E Z, Benzi L, Bertacca A, Cohen P, Del Prato S, Friedman J M, Maffei M. "Identification of cathepsin K as a novel marker of adiposity in white adipose tissue," J Cell Physiol 2003, 195, 309-21.

Another embodiment of the invention is a method of treating glaucoma in a mammal in need thereof, comprising administering to the mammal a therapeutically effective amount of any of the compounds or any of the pharmaceutical compositions described above. Cathepsin K is highly expressed in the iris, ciliary body and retinal pigment epithelium, and as such can be useful in the treatment of glaucoma, see Ortega, J., et al., "Gene Expression of Proteases and Protease Inhibitors in the Human Ciliary Epithelium and ODM-2 cells," Exp. Eye Res (1997) 65, 289-299; International Publication WO 2004/058238 (Alcon, Inc.).

Another embodiment of the invention is a method of treating chronic obstructive pulmonary disease in a mammal in need thereof, comprising administering to the mammal a therapeutically effective amount of any of the compounds or any of the pharmaceutical compositions described above. It is known in the literature that cathepsin K plays a role in lung fibrosis, see Buhling, F., et al, "Pivotal role of cathepsin K in lung fibrosis," Am J Pathol. 2004 June; 164(6):2203-16.

Another embodiment of the invention is a method of treating parasitic infections in a mammal in need thereof, comprising administering to the mammal a therapeutically effective amount of any of the compounds or any of the pharmaceutical compositions described above. It is known in the literature that mammalian cathepsins are related to the papain-like cysteine proteases which play an important role in the life cycle of these parasites. Such parasites are involved in the diseases of malaria, American trypanosomiasis, African trypanosomiasis, leishmaniasis, giardiasis, trichomoniasis, amoebiasis, schistosomiasis, fascioliasis, paragonimiasis and intestinal roundworms, see Lecaille F, Kaleta J, Bromme D., Human and parasitic papain-like cysteine proteases: their role in physiology and pathology and recent developments in inhibitor design. Chem Rev 2002 102, 4459-88.

Another embodiment of the invention is a method of treating severe acute respiratory syndrome (SARS) in a mammal in need thereof, comprising administering to the mammal a therapeutically effective amount of any of the compounds or any of the pharmaceutical compositions described above.

Another embodiment of the invention is a method of treating metastatic bone disease in a mammal in need thereof, comprising administering to the mammal a therapeutically effective amount of any of the compounds or any of the pharmaceutical compositions described above. It is known in the literature that osteoclasts are responsible for bone resorption and that bone destruction and hypercalcemia induced by metastatic tumors are carried out by osteoclasts. Accordingly, the inhibition of osteoclasts can prevent bone destruction and bone metastasis, see Miyamoto, T. and Suda, T., "Differentiation and function of osteoclasts," Keio J Med 2003 March; 52(1): 1-7.

Another embodiment of the invention is a method of preventing metastatic bone disease in a mammal with a primary tumor that carries a risk of bone metastasis, comprising administering to the mammal a therapeutically effective amount of any of the compounds or any of the pharmaceutical compositions described above. It is described in the literature that compounds that inhibit osteoclasts function can prevent tumor cell adhesion to bone, see S. Boissier, M. Ferreras, O. Peyruchaud, S. Magnetto, F. H. Ebetino, M. Colombel, P. Delmas, J.-M. Delaissé and P. Clézardin "Bisphosphonates Inhibit Breast and Prostate Carcinoma Cell Invasion, an Early Event in the Formation of Bone Metastases" Cancer Research 60, 2949-2954, 2000

Another embodiment of the invention is a method of treating hypercalcemia of malignancy or multiple myeloma in a mammal in need thereof, comprising administering to the mammal a therapeutically effective amount of any of the compounds or any of the pharmaceutical compositions described above. It is known in the literature that cathepsin K plays a role in hypercalcemia of malignancy and multiple myeloma, see Faust, J. et al., Multiple myeloma cells and cells of the human osteoclast lineage share morphological and cell surface markers. J Cell Biochem. 1998 Dec. 15; 71(4):559-68; A. lipton, New therapeutic agents for the treatment of bone diseases. Expert Opin Biol Ther. 2005 June; 5(6):817-32.

Another embodiment of the invention is administering to a mammal a therapeutically effective amount of any of the compounds or any of the pharmaceutical compositions described above for the treatment of mammalian diseases associated with cathepsin S including Alzheimer's disease, atherosclerosis, chronic obstructive pulmonary disease, cancer and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. It is known in the literature that cathepsin S activity is associated with the above disease states, see Munger J S, Haass C, Lernere C A, Shi G P, Wong W S, Teplow D B, Selkoe D J, Chapman H A. Lysosomal processing of amyloid precursor protein to A beta peptides: a distinct role for cathepsin S. Biochem J 1995 311, 299-305, Sukhova G K, Zhang Y, Pan J H, Wada Y, Yamamoto T, Naito M, Kodama T, Tsimikas S, Witztum J L, Lu M L, Sakara Y, Chin M T, Libby P, Shi G P. Deficiency of cathepsin S reduces atherosclerosis in LDL receptor-deficient mice. J Clin Invest 2003 111, 897-906, Zheng T, Zhu Z, Wang Z, Homer R J, Ma B, Riese R J Jr, Chapman H A Jr, Shapiro S D, Elias J A. Inducible targeting of IL-13 to the adult lung causes matrix metalloproteinase- and cathepsin-dependent emphysema. J Clin Invest 2000 106, 1081-93, Shi G P, Sukhova G K, Kuzuya M, Ye Q, Du J, Zhang Y, Pan J H, Lu M L, Cheng X W, Iguchi A, Perrey S, Lee A M, Chapman H A, Libby P. Deficiency of the cysteine protease cathepsin S impairs microvessel growth. Circ Res 2003 92, 493-500, Nakagawa T Y, Brissette W H, Lira P D, Griffiths R J, Petrushova N, Stock J, McNeish J D, Eastman S E, Howard E D, Clarke S R, Rosloniec E F, Elliott E A, Rudensky A Y. Impaired invariant chain degradation and antigen presentation and diminished collagen-induced arthritis in cathepsin S null mice. Immunity 1999 10, 207-17.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; a selective estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; Vitamin D; a synthetic Vitamin D analogue; a Nonsteroidal anti-inflammatory drug; a selective cyclooxygenase-2 inhibitor; an inhibitor of interleukin-1 beta; a LOX/COX inhibitor; and the pharmaceutically acceptable salts and mixtures thereof. A preferred combination is a compound of the present invention and an organic bisphosphonate. Another preferred combination is a compound of the present invention and a selective estrogen receptor modulator. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

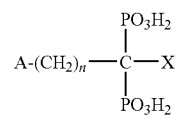

wherein n is an integer from 0 to 7 and wherein A and X are independently selected from the group consisting of H, OH, halogen, $NH_2$, SH, phenyl, $C_1$-$C_{30}$ alkyl, $C_3$-$C_{30}$ branched or cycloalkyl, bicyclic ring structure containing two or three N, $C_1$-$C_{30}$ substituted alkyl, $C_1$-$C_{10}$ alkyl substituted $NH_2$, $C_3$-$C_{10}$ branched or cycloalkyl substituted $NH_2$, $C_1$-$C_{10}$ dialkyl substituted $NH_2$, $C_1$-$C_{10}$ alkoxy, $C_1$-$C_{10}$ alkyl substituted thio, thiophenyl, halophenylthio, $C_1$-$C_{10}$ alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a $C_3$-$C_{10}$ ring.

In the foregoing chemical formula, the alkyl groups can be straight, branched, or cyclic, provided sufficient atoms are selected for the chemical formula. The $C_1$-$C_{30}$ substituted alkyl can include a wide variety of substituents, nonlimiting examples which include those selected from the group consisting of phenyl, pyridyl, furanyl, pyrrolidinyl, imidazonyl, $NH_2$, $C_1$-$C_{10}$ alkyl or dialkyl substituted $NH_2$, OH, SH, and $C_1$-$C_{10}$ alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-$C_1$-$C_{10}$-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronate, which is also known as alendronic acid, 4-amino-1-hydroxybutylidene-1,1-bisphosphonic acid, alendronate sodium or alendronate monosodium trihydrate, 4-amino-1-hydroxybutylidene-1,1-bisphosphonic acid monosodium trihydrate.

Alendronate is described in U.S. Pat. No. 4,922,007, to Kieczykowski et al, issued May 1, 1990; U.S. Pat. No. 5,019,651, to Kieczykowski et al, issued May 28, 1991; U.S. Pat. No. 5,510,517, to Dauer et al, issued Apr. 23, 1996; U.S. Pat. No. 5,648,491, to Dauer et al, issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem.* 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 μg/kg body weight and preferably about 10 to about 2000 μg/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing, hi a once weekly dosing regimen, alendronate monosodium trihydrate would be administered at dosages of 35 mg/week or 70 mg/week.

"Selective estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulveslrant, 4-[7-(2,2-dimethyl-1-oxopropoxy- 4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

An "estrogen receptor beta modulator" is a compound that selectively agonizes or antagonizes estrogen receptor beta (ERβ Agonizing ERβ increases transcription of the tryptophan hydroxylase gene (TPH, the key enzyme in serotonin synthesis) via an ERβ mediated event. Examples of estrogen receptor beta agonists can be found in PCT International publication WO 01/82923, which published on Nov. 8, 2001, and WO 02/41835, which published on May 20, 2002, both of which are hereby incorporated by reference in their entirety.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163-172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

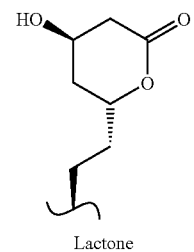

Lactone

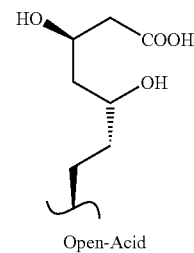

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the αvβ5 integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. H.N. Lode and coworkers in PNAS USA 96: 1591-1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The α and β integrin subunits interact non-covalently and bind extracellular matrix ligands in a divalent cation-dependent manner. The most abundant integrin on osteoclasts is $\alpha_v\beta_3$ ($>10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690-709 (1993). Studies have demonstrated the clinical benefits of parathyroid hormone in stimulating bone formation and thereby increasing bone mass and strength. Results were reported by R M Neer et al., in New Eng J Med 344 1434-1441 (2001).

In addition, parathyroid hormone-related protein fragments or analogues, such as PTHrP-(1-36) have demonstrated potent anticalciuric effects [see M. A. Syed et al., "Parathyroid hormone-related protein-(1-36) stimulates renal tubular calcium reabsorption in normal human volunteers: implications for the pathogenesis of humoral hypercalcemia of malignancy," JCEM 86: 1525-1531 (2001)] and may also have potential as anabolic agents for treating osteoporosis.

"Vitamin D" includes, but is not limited to, vitamin $D_3$ (cholecalciferol) and vitamin $D_2$ (ergocalciferol), which are naturally occurring, biologically inactive precursors of the hydroxylated biologically active metabolites of vitamin D: 1α-hydroxy vitamin D; 25-hydroxy vitamin D, and 1α,25-dihydroxy vitamin D. Vitamin $D_2$ and vitamin $D_3$ have the same biological efficacy in humans. When either vitamin $D_2$ or $D_3$ enters the circulation, it is hydroxylated by cytochrome $P_{450}$-vitamin D-25-hydroxylase to give 25-hydroxy vitamin D. The 25-hydroxy vitamin D metabolite is biologically inert and is further-hydroxylated in the kidney by cytochrome P450-monooxygenase, 25 (OH) D-1α-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

1,25-dihydroxy vitamin D is thought to be responsible for the effects of vitamin D on calcium and bone metabolism. The 1,25-dihydroxy metabolite is the active hormone required to maintain calcium absorption and skeletal integrity. Calcium homeostasis is maintained by 1,25-dihydroxy vitamin D by inducing monocytic stem cells to differentiate into osteoclasts and by maintaining calcium in the normal range, which results in bone mineralization by the deposition of calcium hydroxyapatite onto the bone surface, see Holick, M F, Vitamin D photobiology, metabolism, and clinical applications, In: DeGroot L, Besser H, Burger H G, eg al., eds. *Endocrinology*, 3$^{rd}$ ed., 990-1013 (1995). However, elevated levels of 1α,25-dihydroxy vitamin $D_3$ can result in an increase of calcium concentration in the blood and in the abnormal control of calcium concentration by bone metabolism, resulting in hypercalcemia. 1α,25-dihydroxy vitamin $D_3$ also indirectly regulates osteoclastic activity in bone metabolism and elevated levels may be expected to increase excessive bone resorption in osteoporosis.

"Synthetic vitamin D analogues" includes non-naturally occurring compounds that act like vitamin D.

"Nonsteroidal anti-inflammatory drugs" or NSAIDs, inhibit the metabolism of arachidonic acid to proinflammatory prostaglandins via cyclooxygenase (COX)-1 and COX-2. Nonlimiting examples of NSAIDs include: aspirin, ibuprofen, naproxen, diclofenac, etodolac, fenoporfen, flubiprofen, indomethacin, ketoprofen, ketorolac, meloxicam, nabumetone, oxaprozin, piroxicam, sulindac, tolmetin, diflunisal, meclofenamate and phenylbutazone.

A "selective cyclooxygenase-2 inhibitor," or COX-2 inhibitor, refers to a type of nonsteroidal anti-inflammatory drug (NSAID), that inhibit the COX-2 coenzyme, which contributes to pain and inflammation in the body. Nonlimiting examples of COX-2 inhibitos include: celecoxib, etoricoxib, parecoxib, rofecoxib, valdecoxib and lumiracoxib.

An "inhibitor of interleukin-1 beta" or IL-1β refers to in inhibitors of IL-1, which is a soluble factor produced by monocytes, macrophages, and other cells which activates T-lymphocytes and potentiates their response to mitogens or antigens. Nonlimiting examples of IL-1B inhibitors include diacerein and rhein.

A "LOX/COX inhibitor" refers to an inhibitor or all three of the major enzymes involved in arachidonic acid pathway—namely, 5-LOX, COX-1 and COX-2. A nonlimiting example of a LOX/COX inhibitor is licofelone.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation Of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for a cathepsin dependent condition. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The compounds of the present invention can be used in combination with other agents useful for treating cathepsin-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the instantly claimed compounds in combination with a second agent selected from: an organic bisphosphonate; a selective estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; Vitamin D; a synthetic Vitamin D analogue; a Nonsteroidal anti-inflammatory drug; a selective cyclooxygenase-2 inhibitor; an inhibitor of interleukin-1 beta; a LOX/COX inhibitor and the pharmaceutically acceptable salts and mixtures thereof.

These and other aspects of the invention will be apparent from the teachings contained herein.

DEFINITIONS

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

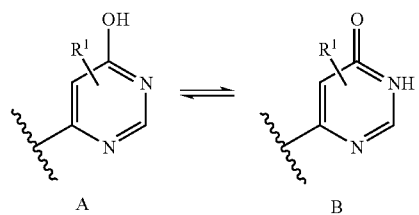

When any variable (e.g. $R^1$, $R^2$, $R^3$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having one to ten carbon atoms unless otherwise specified. For example, $C_1$-$C_{10}$, as in "$C_1$-$C_{10}$ alkyl" is defined to include groups having 1, 2, 3, 4, 5, 6, 7, 8, 9 or 10 carbons in a linear, branched, or cyclic arrangement. For example, "$C_1$-$C_{10}$ alkyl" specifically includes methyl, ethyl, propyl, butyl, pentyl, hexyl, heptyl, octyl, nonyl, decyl, and so on.

The term "haloalkyl" means an alkyl radical as defined above, unless otherwise specified, that is substituted with one to five, preferably one to three halogen. Representative examples include, but are not limited to trifluoromethyl, dichloroethyl, and the like.

As used herein, "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo.

In certain instances, substituents may be defined with a range of carbons that includes zero, such as ($C_0$-$C_6$)alkylenearyl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Phamu Sci.*, 1977:66:1-19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts Of the acidic compounds are formed by reactions with the appropriate inorganic or organic base.

For purposes of this specification, the following abbreviations have the indicated meanings:

| | |
|---|---|
| BuLi = | normal butyl lithium |
| $CBr_4$ = | tetrabromomethane |
| $CH_2Cl_2$ = | methylene chloride |
| $CHCl_3$ = | chloroform |
| $(CH_3O)_2CO$ = | dimethyl carbonate |
| DAST = | diethylaminosulfur trifluoride |
| DIBAL—H = | diisobutylaluminum hydride |
| DIPEA = | diisopropylethylamine |
| DMF = | N,N-dimethylformamide |
| DMSO = | dimethylsulfoxide |
| $Et_3N$ = | triethylamine |
| EtOH = | ethanol |
| $KH_2PO_4$ = | potassium dihydrogenphosphate |
| HCl = | hydrochloric acid |
| LG = | leaving group |

-continued

| | |
|---|---|
| MeOH = | methanol |
| MgBr = | magnesium bromide |
| MgSO$_4$ = | magnesium sulfate |
| Na$_2$CO$_3$ = | sodium carbonate |
| NaOMe = | sodium methoxide |
| Na$_2$SO$_4$ = | sodium sulfate |
| PCl$_5$ = | phosphorous pentachloride |
| PdCl$_2$(dppf) = | [1,1'-bis(diphenylphosphino)ferrocene]dichloropalladium(II) |
| PG = | protecting group |
| PPh$_3$ = | triphenylphosphine |
| Pr$_2$NEt = | N,N-diisopropylethylamine |
| PyBOP = | benzotriazol-1-yloxytris(pyrrolidino)phosphonium-hexafluorophosphate |
| rt = | room temperature |
| sat. aq. = | saturated aqueous |
| TBAF = | tetrabutylammonium fluoride |
| TfO = | trifluoromethanesulfonate |
| THF = | tetrahydrofuran |
| tlc = | thin layer chromatography |
| TMSBr = | bromotrimethylsilane |
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |

Schemes

Compounds of the present invention can be prepared according to Scheme 1, as indicated below. A protected 4-hydroxy-2-butenoic acid, that is coupled to an acceptable chiral auxiliary, undergoes a Diels-Alder reaction with an appropriate 2-substituted-1,3-butadiene at low temperatures in the presence of a suitable Lewis acid catalyst. Hydrolysis of the intermediate diastereomerically-enriched enol-ether with aqueous acid generates a ketone that is converted to the corresponding gem-dihalogenated compound ($R^1$, $R^2$=chloro or fluoro) by treatment with a suitable halogenating agent such as DAST, PCl$_5$ or hydrazine/CuCl$_2$/Et$_3$N. Alternatively, the auxiliary can be removed prior to the introduction of the halogen substituents. Reductive removal of the chiral auxiliary liberates an enantiomerically-enriched alcohol that is oxidized to an aldehyde and reacted with a metallated derivative of 4-(methylthio)-phenyl acetic acid ester. Oxidation of the resulting aldol gives a keto-ester that is reacted with an N-monosubstituted-hydrazine, in the presence of an appropriate catalyst, to yield a hydroxypyrazole. The hydroxyl group is then converted to a suitable leaving group (e.g. chloro, bromo iodo or alkyl/aryl sulfonate) and the methyl thioether is oxidized to the corresponding methyl sulfone. Treatment with hydrogen in the presence of palladium on charcoal results in reductive removal of the leaving group. Subsequent cleavage of the protecting group liberates a primary alcohol that is oxidized to the corresponding carboxylic acid and coupled to 1-aminocyclopropanecarbonitrile to afford compounds of the current invention.

SCHEME 1

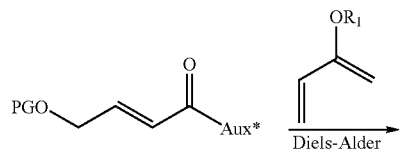

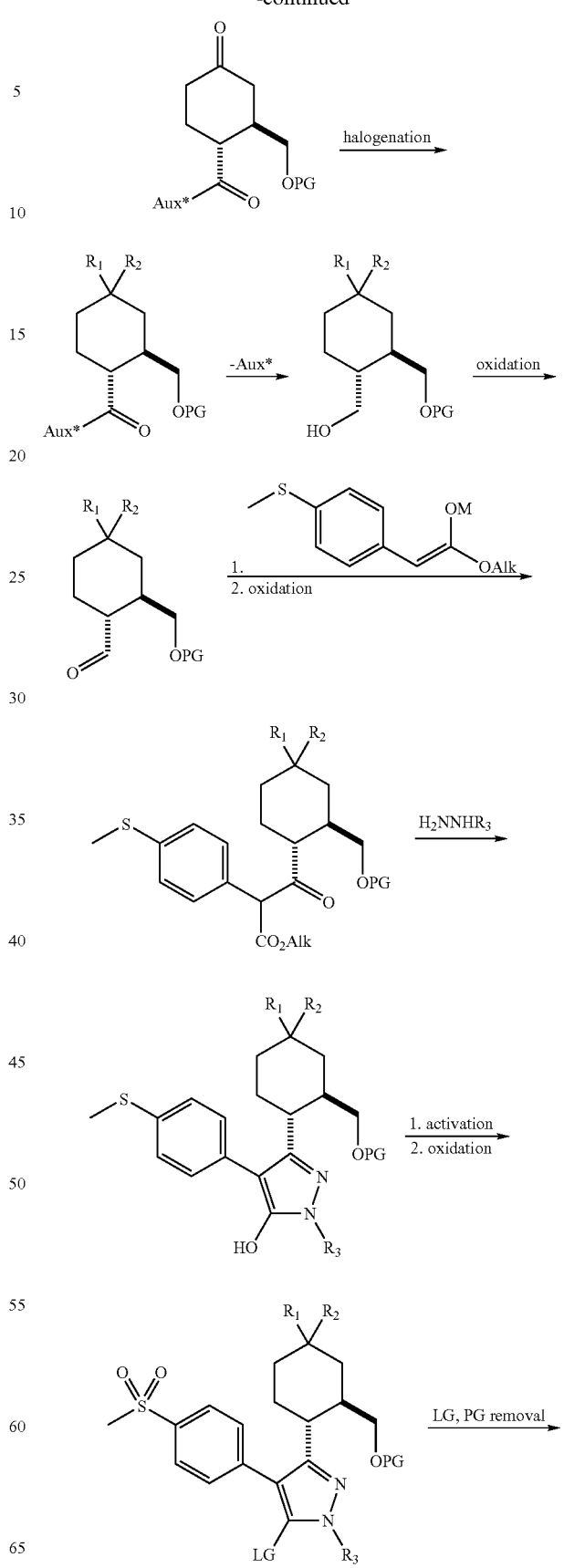

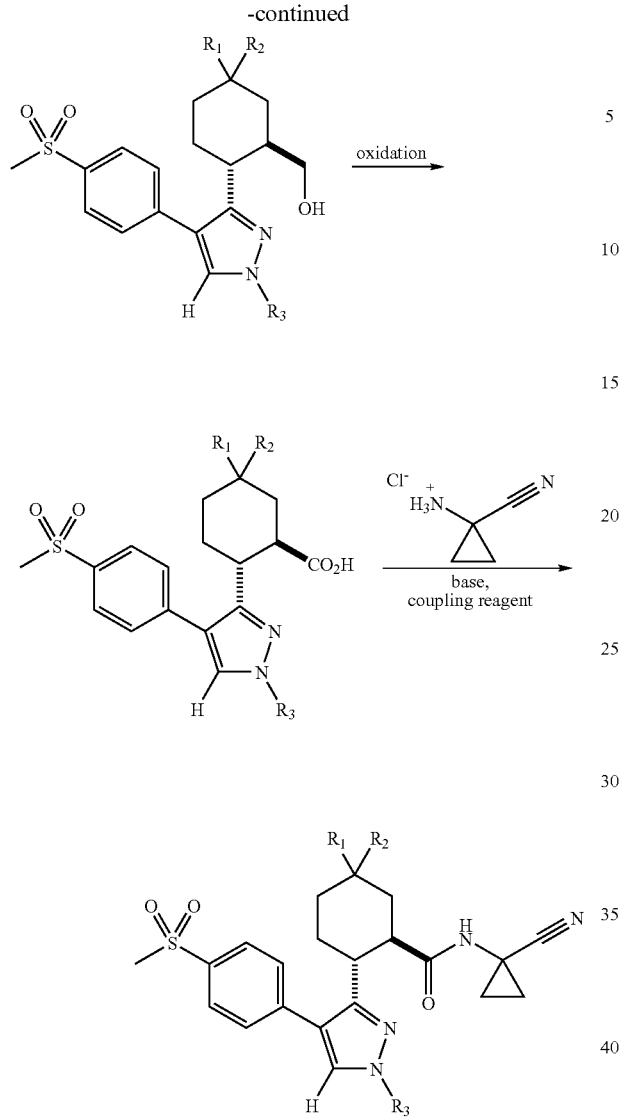

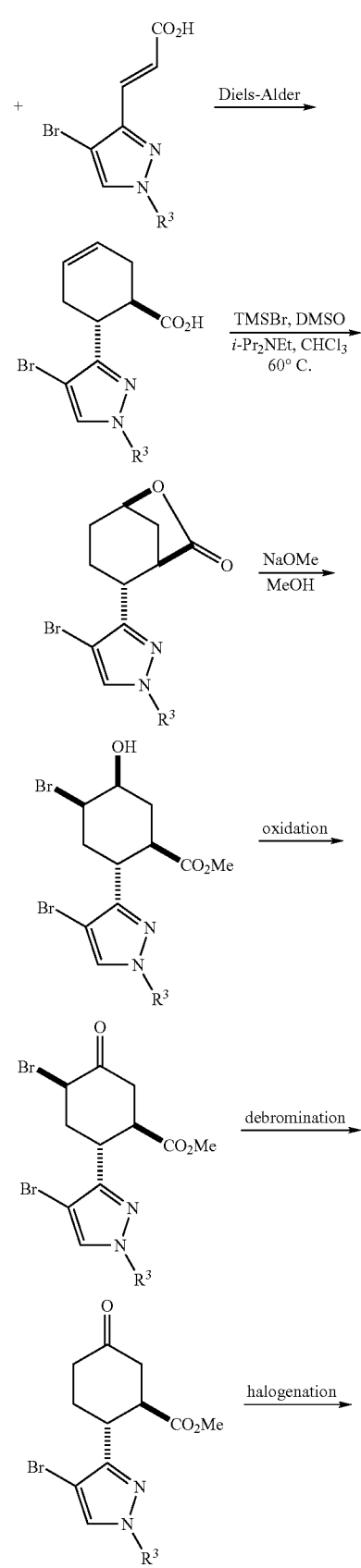

SCHEME 2

Compounds of the present invention may also be prepared according to Scheme 2, as indicated below. Thus, the Diels-Alder adduct from 1,3-butadiene and an N¹-substituted-(2E)-3-(4-bromo-1H-pyrazol-3-yl)prop-2-enoic acid (see example 4 in WO 2005/000800) can be converted to a bromolactone with TMSBr/DMSO/DIPEA (see Miyashita, K.; Tanaka, A.; Mizuno, H.; Tanaka, M.; Iwata, C. *J. Chem. Soc. Perkin Trans. I,* 1994, 847-851). Methoxide catalyzed opening of the lactone affords a bromohydroxyester that is converted to the corresponding ketone by oxidation of the alcohol followed by reductive debromination, with zinc for example. This ketone is subsequently converted to the corresponding gem-difluoro ($R^1$,$R^2$=F) or gem-dichloro ($R^1$,$R^2$=Cl) compounds by treatment with DAST or hydrazine/CuCl$_2$/Et$_3$N (see Takeda, T.; Sasaki, R.; Yamauchi, S.; Fujiwara, T. *Tetrahedron* 1997, 53, 557) respectively. Saponification of the ester functionality with aqueous base, coupling with 1-amino-cyclopropanecarbonitrile, and oxidation of the methylthioether to the corresponding methylsulfone affords compounds of the current invention.

-continued

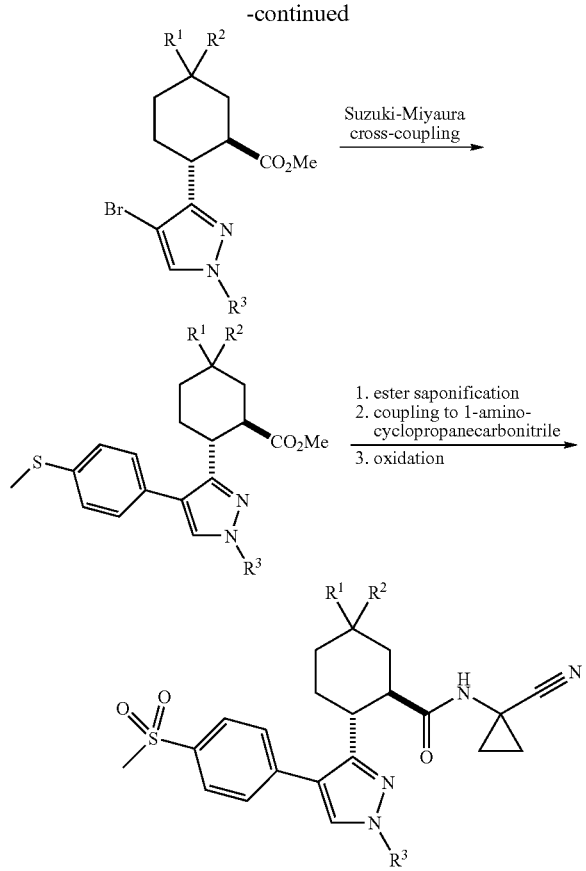

The following examples describe the synthesis of selected compounds of the current invention and are included for illustrative purposes and do not limit the scope of the invention in any way.

EXAMPLE 1

(1R,2R)-N-(1-Cyanocyclopropyl)-5,5-difluoro-2-[4-[4-(methylsulfonyl)phenyl]-1-(2,2,2-trifluoroethyl)-1H-pyrazol-3-yl]cyclohexanecarboxamide

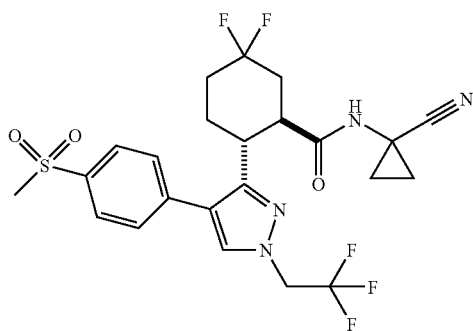

Diisopropylethylamine (51 mL, 290 mmol) was added slowly to a mechanically stirred, 0° C. slurry composed of {2-[(4R)-4-benzyl-2-oxo-1,3-oxazolidin-3-yl]-2-oxoethyl}phosphonate (94.8 g, 267 mmol; see Shapiro, G; Chengzhi, C. Tetrahedron Lett. 1992, 33, 2447) and dry lithium chloride (12.5 g, 280 mmol) in acetonitrile (260 mL). After stirring for 10 min, a solution of 2-benzyloxyacetaldehyde (40.0 g, 267 mmol) in acetonitrile (20 mL) was added dropwise over 10 min. The cooling bath was then removed and the reaction mixture was stirred at rt for 12 h before being partitioned between ether and water and the layers separated The aqueous phase was extracted with additional ether and the combined organic phases (700 mL total) were stirred at rt with 2M HCl (350 mL) for 1 h. The organic phase was then washed with saturated NaCl and NaHCO$_3$ aqueous solutions, followed by drying over a mixture of Na$_2$SO$_4$ and MgSO$_4$, and concentration in vacuo. Flash chromatography of the residue on silica gel eluting with 10/90 acetone/benzene yielded (4R)-4-benzyl-3-[(2E)-4-(benzyloxy)but-2-enoyl]-1,3-oxazolidin-2-one as a colorless solid upon trituration with ether. $^1$H NMR (500 MHz, d$_6$-acetone) δ 7.57 (1H, d, J= 15.6 Hz), 7.43-7.27 (10H, m), 7.21-7.15 (1H, m), 4.84 (1H, t, J= 8.2 Hz), 4.64 (2H, s), 4.43 (1H, t, J= 8.5 Hz), 4.32 (2H, m), 4.29 (1H, dd, J= 2.9, 8.9 Hz), 3.24 (1H, dd, J= 3.1, 13.5 Hz), 3.03 (1H, dd, J= 8.4, 13.5 Hz).

A solution of Et$_2$AlCl (1.8 M in toluene, 158 mL, 284 mmol) was added slowly down the flask wall to a −78° C. solution of (4R)-4-benzyl-3-[(2E)-4-(benzyloxy)but-2-enoyl]-1,3-oxazolidin-2-one (70.9 g, 202 mmol) in CH$_2$Cl$_2$ (200 mL). After 10 min, a solution of 2-(trimethylsilyl)oxy-1,3,-butadiene (100 g, 700 mmol) in CH$_2$Cl$_2$ (120 mL) was introduced in the same manner over a period of 15 min. Stirring was continued at −78° C. overnight (18 h). The reaction flask contents were then warmed to −50° C. and a solution composed of THF (150 mL) and 6M HCl (150 mL) was CAREFULLY added dropwise over 45 min followed by stirring at rt for 1 h. Water, ethyl acetate and Celite® were then added and the mixture was filtered through a Celite® pad. The filtrate was transferred to a separatory funnel and the layers were separated. The organic phase was washed with saturated NaCl aqueous solution, dried over a mixture of Na$_2$SO$_4$ and MgSO$_4$ and concentrated in vacuo. Flash chromatography of the residue on silica gel eluting with 13/87 ethyl acetate/benzene gave (4R)-4-benzyl-3-({(1R,2R)-2-[(benzyloxy)methyl]-4-oxocyclohexyl}carbonyl)-1,3-oxazolidin-2-one as a colorless solid. $^1$H NMR (400 MHz, d$_6$-acetone) δ 7.38-7.32 (6H, m), 7.31-7.25 (4H, m), 4.59-4.53 (1H, m), 4.47 (2H, q, J= 8.5 Hz), 4.19 (1H, dd, J= 3.0, 9.0 Hz), 4.15-4.09 (1H, m), 4.03 (1H, t, J= 8.6 Hz), 3.53-3.47 (2H, m), 3.13 (1H, dd, J= 3.4, 13.6 Hz), 2.97 (1H, dd, J= 8.2, 13.5 Hz), 2.70-2.60 (1H, m), 2.54-2.46 (1H, m), 2.44 (2H, d, J= 9.3 Hz), 2.41-2.29 (2H, m), 1.92-1.82 (1H, m).

Deoxofluor® (21 mL, 110 mmol) was added slowly over 5 min to a 0° C. solution of (4R)-4-benzyl-3-({(1R,2R)-2-[(benzyloxy)methyl]-4-oxocyclohexyl}carbonyl)-1,3-oxazolidin-2-one (18.7 g, 44.4 mmol) in CH$_2$Cl$_2$ (100 mL). After 2 h at this temperature, the reaction was quenched by the careful addition of an equal volume of ice water. After separation of the phases, the aqueous layer was extracted with CH$_2$Cl$_2$ and the combined organics were washed with water and saturated aqueous NaHCO$_3$, and dried (Na$_2$SO$_4$). The methylene chloride solution containing the crude product was concentrated to a volume of 100 mL and treated with purified m-chloroperbenzoic acid (6.0 g, 35 mmol) with stirring at rt for 3 h. Additional CH$_2$Cl$_2$ (100 mL) was then added followed by Me$_2$S (3 mL) and Ca(OH)$_2$ (20 g) with stirring at rt for 15 min. The slurry was filtered through Celite® and the filtrate was concentrated in vacuo. Flash chromatography of the residue on silica gel eluting with 1/3 ethyl acetate/hexanes yielded (4R)-4-benzyl-3-({(1R,2R)-2-[(benzyloxy)methyl]-4,4-difluorocyclohexyl}carbonyl)-1,3-oxazolidin-2-one as a thick, colorless syrup. $^1$H NMR δ (500 MHz, d$_6$-acetone) 7.36-7.32 (6H, m), 7.26 (4H, dd, J=7.3, 24.1 Hz), 4.54-4.50

(1H, m), 4.48-4.42 (2H, m), 4.19-4.15 (1H, m), 3.99 (1H, t, J= 8.6 Hz), 3.80-3.74 (1H, m), 3.47 (2H, d, J= 5.5 Hz), 3.13-3.09 (1H, m), 2.94 (1H, dd, J= 8.2, 13.5 Hz), 2.56-2.48 (1H, m), 2.26-2.12 (3H, m), 1.95-1.71 (3H, m).

A solution of n-BuLi (2.5M in hexanes, 10 mL) was added slowly to a solution of benzyl mercaptan (3.6 mL, 40 mmol) in THF (40 mL) at 0° C. The resulting pale-yellow solution was stirred at 0° C. for 10 min prior to the introduction of (4R)-4-benzyl-3-({(1R,2R)-2-[(benzyloxy)methyl]-4,4-difluorocyclohexyl}carbonyl)-1,3-oxazolidin-2-one (8.52 g, 19.2 mmol) as a solution in THF (30 mL). After 10 min, a solution of LiAlH$_4$ (1.0 M in THF, 22 mL) was slowly added to the reaction mixture with continued stirring at 0° C. for 45 min. Ice water was then slowly added to destroy excess hydride followed by 6M HCl (20 mL) to pH 1. The mixture was extracted with two portions of ethyl acetate and the combined organics were washed with saturated aqueous NaCl and dried over Na$_2$SO$_4$. Concentration in vacuo and flash chromatography of the residue on silica gel eluting with 45/55 ethyl acetate/hexanes afforded {(1R,2R)-2-[(benzyloxy)methyl]-4,4-difluorocyclohexyl}methanol as a thick, colorless syrup. $^1$H NMR (500 MHz, d$_6$-acetone) δ 7.36 (4H, m), 7.34-7.28 (1H, m), 4.56-4.49 (2H, m), 3.67-3.53 (5H, m), 2.20-2.12 (1H, m), 2.09-2.02 (1H, m), 1.91-1.71 (4H, m), 1.58-1.50 (2H, m).

Dess-Martin periodinane (9.84 g, 23.2 mmol) was added to a solution of (1R,2R)-2-[(benzyloxy)methyl]-4,4-difluorocyclohexyl}methanol (5.01 g, 20.2 mmol) in CH$_2$Cl$_2$ (50 mL) at 0° C. The mixture was stirred at 0° C. for 5 min, then at rt for 1 h. Ethyl acetate (100 mL), a saturated aqueous solution of NaHCO$_3$ (100 mL), water and Na$_2$S$_2$O$_3$.5H$_2$O (28.9 g, 120 mmol) were added with stirring at rt for 30 min. The layers were separated and the aqueous phase was extracted with additional ethyl acetate. The combined organics were washed with saturated NaCl aqueous solution and dried (Na$_2$SO$_4$). Concentration in vacuo and flash chromatography on silica gel eluting with 16/84 ethyl acetate/hexanes gave (1R,2R)-2-[(benzyloxy)methyl]-4,4-difluorocyclohexanecarbaldehyde as a colorless liquid. $^1$H NMR (500 MHz, d$_6$-acetone) δ 9.66 (1H, d, J= 3.0 Hz), 7.37-7.33 (4H, m), 7.31-7.29 (1H, m), 4.52 (2H, m), 3.55 (1H, dd, J= 4.8, 9.3 Hz), 3.51-3.45 (1H, m), 2.43-2.33 (2H, m), 2.20-2.12 (2H, m), 1.98-1.66 (4H, m).

A 2.1 M solution of n-BuLi (11 mL, 23 mmol) in hexanes was added slowly to a 0° C. solution of diisopropylamine (4.0 mL, 28 mmol) in THF (10 mL). Stirring was continued at this temperature for an additional 10 min prior to cooling to −78° C. A solution of ethyl [4-(methylthio)phenyl]acetate (4.64 g, 18.9 mmol) in THF (15 mL) was then introduced and the mixture was stirred at −78° C. for 10 min, −40° C. for 10 min and finally at 0° C. for 5 min. The solution was recooled to −78° C. and a solution of (1R,2R)-2-[(benzyloxy)methyl]-4,4-difluorocyclohexanecarbaldehyde (4.64 g, 18.9 mmol) in THF (15 mL) was added down the flask wall over 5 min. Stirring was continued at −78° C. for 30 min then at −40° C. for 1 h. A saturated aqueous solution of NH$_4$Cl was added and the reaction mixture was warmed to rt and partitioned between ethyl acetate and water. The organic phase was washed with saturated aqueous NaCl solution and dried over Na$_2$SO$_4$. Concentration in vacuo and flash chromatography on silica gel eluting with 3/7 ethyl acetate/hexanes gave ethyl 3-{2-[(benzyloxy)methyl]-4,4-difluorocyclohexyl}-3-hydroxy-2-[4-(methylthio)phenyl]propanoate as a faint-yellow, thick syrup. $^1$H NMR (400 MHz, d$_6$-acetone) δ 7.43-7.33 (5H, m), 7.33-7.29 (2H, m), 7.15-7.11 (2H, m), 4.66 (1H, m), 4.57-4.49 (2H, m), 4.16-4.00 (2H, m), 3.74 (2H, d, J= 10.7 Hz), 3.45 (1H, dd, J=2.8, 9.5 Hz), 2.46 (3H, s), 1.84-1.75 (2H, m) 13.5 Hz), 1.73-1.63 (1H, m), 1.17 (3H, t, 7= 7.1 Hz).

Oxalyl chloride (2.9 mL, 34 mmol) was added dropwise to a −78° C. solution of dimethyl sulfoxide (2.9 mL, 41 mmol) in CH$_2$Cl$_2$ (40 mL). Stirring was continued at −78° C. for an additional 10 min prior to the slow introduction down the flask wall of a solution of ethyl 3-{2-[(benzyloxy)methyl]-4,4-difluorocyclohexyl}-3-hydroxy-2-[4-(methylthio)phenyl]propanoate (5.09 g, 10.6 mmol) and triethylamine (16 mL, 120 mmol) in CH$_2$Cl$_2$ (40 mL). The mixture was then held at −78° C. for 10 min followed by rapid warming to rt before being poured into 2 M HCl in a separatory funnel. The layers were shaken and separated, and the aqueous phase was extracted with an additional portion of CH$_2$Cl$_2$. The combined organics were washed with water, dried (Na$_2$SO$_4$) and concentrated. Flash chromatography of the residue on silica gel eluting with 1/4 ethyl acetate/hexanes afforded ethyl 3-{2-[(benzyloxy)methyl]-4,4-difluorocyclohexyl}-2-[4-(methylthio)phenyl]-3-oxopropanoate as a thick, tan colored syrup.

A slurry composed of ethyl 3-{2-[(benzyloxy)methyl]-4,4-difluorocyclohexyl}-2-[4-(methylthio)phenyl]-3-oxopropanoate (4.43 g, 9.31 mmol), 1,1,2,2-tetrachloroethane (100 mL) and MgSO$_4$ (50 g) was heated at 120° C. for 3 days. The mixture was then cooled in ice and water (200 mL) was added followed by 6 M HCl to pH 1. The layers were separated and the aqueous phase was extracted with two portions of CH$_2$Cl$_2$. The combined organics were washed with water, dried (Na$_2$SO$_4$) and concentrated. Flash chromatography on silica gel eluting with 15/85 acetone/benzene yielded 3-{(1R,2R)-2-[(benzyloxy)methyl]-4,4-difluorocyclohexyl}-4-[4-(methylthio)phenyl]-1-(2,2,2-trifluoroethyl)-1H-pyrazol-5-ol as a yellow foam. $^1$H NMR (400 MHz, d$_6$-acetone) δ 9.66 (1H, br s), 7.36-7.26 (5H, m), 7.20 (4H, m), 4.78 (1H, m), 4.37 (1H, d, J= 11 Hz), 4.30 (1H, d, J= 11 Hz), 3.38 (2H, m), 2.75-2.92 (3H, m), 2.50 (3H, s), 2.41 (1H, m), 2.23 (1H, m), 2.00-1.75 (4H, m).

A solution of 3-{(1R,2R)-2-[(benzyloxy)methyl]-4,4-difluorocyclohexyl}-4-[4-(methylthio)phenyl]-1-(2,2,2-trifluoroethyl)-1H-pyrazol-5-ol (3.95 g, 7.5 mmol) and pyridine (0.95 mL, 12 mmol) in CH$_2$Cl$_2$ (30 mL) was cooled to 0° C. and treated with trifluoromethanesulfonic acid anhydride (1.5 mL, 9.2 mmol). After 15 min at 0° C., the reaction vessel contents were partitioned between water and CH$_2$Cl$_2$ and the layers were separated. The aqueous layer was extracted with an additional portion of CH$_2$Cl$_2$ and the combined organics were washed with water, dried (Na$_2$SO$_4$) and concentrated. Flash chromatography on silica gel eluting with 15/85 ethyl acetate/hexanes gave 3-{(1R,2R)-2-[(benzyloxy)methyl]-4,4-difluorocyclohexyl}-4-[4-(methylthio)phenyl]-1-(2,2,2-trifluoroethyl)-1H-pyrazol-5-yl trifluoromethanesulfonate as a faint-yellow solid.

Purified m-chloroperoxybenzoic acid (2.62 g, 15.2 mmol) was added in one portion at 0° C. to a solution of 3-{(1R,2R)-2-[(benzyloxy)methyl]-4,4-difluorocyclohexyl}-4-[4-(methylthio)phenyl]-1-(2,2,2-trifluoroethyl)-1H-pyrazol-5-yl trifluoromethanesulfonate (4.36 g, 6.63 mmol) in CH$_2$Cl$_2$ (40 mL). The resulting slurry was stirred at 0° C. for 5 min then at rt for 30 min before being treated diluted with CH$_2$Cl$_2$ (40 mL) and treated with dimethyl sulphide (0.25 mL) and Ca(OH)$_2$ (9.0 g, 160 mmol). After stirring at rt for 10 min, the mixture was filtered (Celite®) and the filtrate was concentrated in vacuo. Flash chromatography on silica gel eluting with 3/7 ethyl acetate/hexanes gave 3-{(1R,2R)-2-[(benzyloxy)methyl]-4,4-difluorocyclohexyl}-4-[4-(methylsulfonyl)phenyl]-1-(2,2,2-trifluoroethyl)-1H-pyrazol-5-yl trifluoromethanesulfonate as a colorless foam. $^1$H NMR δ $^1$H NMR (400 MHz, d₆-acetone) δ 7.97 (2H, d, J= 8.1 Hz), 7.70 (2H, d, J= 8.1 Hz), 7.36-7.26 (3H, m), 7.19 (2H, m), 5.17-5.07 (2H, m), 4.35 (1H, d, J= 11.9 Hz), 4.28 (1H, d, J= 11.9 Hz), 3.37-3.27 (2H, m), 3.13 (3H, s), 2.97 (1H, m) 2.41 (1H, m), 2.22 (1H, m), 2.10-2.02 (2H, m), 2.00-1.80 (3H, m).

A mixture of 3-{(1R,2R)-2-[(benzyloxy)methyl]-4,4-difluorocyclohexyl}-4-[4-(methylsulfonyl)phenyl]-1-(2,2,2-trifluoroethyl)-1H-pyrazol-5-yl trifluoromethanesulfonate (4.54 g, 6.58 mmol) and 10% palladium on charcoal (2.20 g) were stirred together in ethyl acetate (60 mL) under an atmosphere of hydrogen gas at rt for 16 h. Filtration through Celite®, concentration of the filtrate and flash chromatography on silica gel eluting with 45/55 ethyl acetate/hexanes yielded 3-{(1R,2R)-2-[(benzyloxy)methyl]-4,4-difluorocyclohexyl}-4-[4-(methylsulfonyl)phenyl]-1-(2,2,2-trifluoroethyl)-1H-pyrazole as a colorless, thick syrup.

A mixture of 3-{(1R,2R)-2-[(benzyloxy)methyl]-4,4-difluorocyclohexyl}-4-[4-(methylsulfonyl)phenyl]-1-(2,2,2-trifluoroethyl)-1H-pyrazole (2.15 g, 3.97 mmol) and Pearlman's catalyst (1.0 g) were stirred together in ethyl acetate (50 mL) containing acetic acid (5 mL) under an atmosphere of hydrogen at rt for 20 h. The reaction mixture was then filtered through a Celite® pad and the filtrate was washed with saturated aqueous solutions of NaHCO₃ and NaCl before drying over Na₂SO₄. Solvent removal in vacuo yielded {(1R,2R)-5,5-difluoro-2-[4-[4-(methylsulfonyl)phenyl]-1-(2,2,2-trifluoroethyl)-1H-pyrazol-3-yl]cyclohexyl}methanol as a faint-yellow, thick syrup. ¹H NMR (400 MHz, acetone d₆) δ 8.06 (1H, s), 7.96 (2H, d, J= 8.4 Hz), 7.79 (2H, d, J= 8.4 Hz), 5.08 (2H, q, J=8.8 Hz), 3.70 (1H, m), 3.47 (1H, m), 3.36 (1H, m), 3.16 (3H, s), 3.09 (1H, m), 2.38 (1H, m), 2.25 (1H, m), 2.15-1.30 (5H, m).

A solution of {(1R,2R)-5,5-difluoro-2-[4-[4-(methylsulfonyl)phenyl]-1-(2,2,2-trifluoroethyl)-1H-pyrazol-3-yl]cyclohexyl}methanol (1.64 g, 3.63 mmol) in acetone (40 mL) was treated at 0° C. with Jones reagent (3.8 mL) followed by stirring at rt for 30 min. Water was added and the mixture was extracted with two portions of ethyl acetate. The combined organics were washed twice with water then with a saturated aqueous solution of NaCl before drying over Na₂SO₄. Concentration in vacuo gave (1R,2R)-5,5-difluoro-2-[4-[4-(methylsulfonyl)phenyl]-1-(2,2,2-trifluoroethyl)-1H-pyrazol-3-yl]cyclohexanecarboxylic acid as a faint-yellow foam.

Diisopropylethylamine (3.2 mL, 18 mmol) was added in one portion to a solution of (1R,2R)-5,5-difluoro-2-[4-[4-(methylsulfonyl)phenyl]-1-(2,2,2-trifluoroethyl)-1H-pyrazol-3-yl]cyclohexanecarboxylic acid (1.69 g, 3.63 mmol), 1-aminocyclopropanecarbonitrile hydrochloride (1.16 g, 9.83 mmol) and HATU (1.72 g, 4.53 mmol) in DMF (10 mL) with stirring at rt for 2.5 h. The reaction vessel contents were then partitioned between ethyl acetate and water and the layers were separated. The aqueous phase was extracted with additional ethyl acetate and the combined organics were washed with 2 M HCl, 10% Na₂CO₃ and saturated NaCl aqueous solutions, followed by drying over Na₂SO₄. Concentration in vacuo and flash chromatography on silica gel eluting with 22.5/77.5 acetone/benzene provided the title compound as a colorless powder upon trituration with a mixture of hexanes and ether. ¹H NMR (400 MHz, acetone d₆) δ 8.03 (1H, s), 7.99 (2H, d, J= 8.5 Hz), 7.83 (1H, overlapped m), 7.81 (2H, d, J= 8.5 Hz), 5.05 (2H, q, J= 8.8 Hz), 3.36 (1H, m), 3.18 (3H, s), 3.12 (1H, m), 2.23 (1H, m), 2.15-1.95 (4H, m), 1.79 (1H, m), 1.37 (2H, m), 1.05 (1H, m), 0.81 (1H, m). MS: (+ESI) 531.0 [M+H]⁺.

EXAMPLE 2

(1R,2R)-N-(1-Cyanocyclopropyl)-5,5-dichloro-2-[4-[4-(methylsulfonyl)phenyl]-1-(2,2,2-trifluoroethyl)-1H-pyrazol-3-yl]cyclohexanecarboxamide

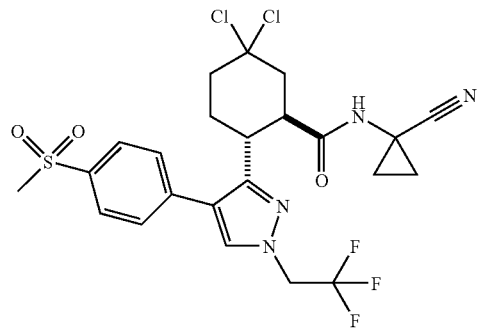

Trimethylsilyl trifluoromethanesulfonate (2.5 mL) was added dropwise to a 0° C. solution of (4R)-4-benzyl-3-({(1R,2R)-2-[(benzyloxy)methyl]-4-oxocyclohexyl}carbonyl)-1,3-oxazolidin-2-one (57.89 g, 138 mmol) and 1,2-bis-(trimethylsilyloxy)ethane (35.4 g, 172 mmol) in CH₂Cl₂ (400 mL) followed by stirring at rt for 4 h. Triethylamine (3 mL) was then added at 0° C. and the mixture was washed with saturated aqueous NaHCO₃ solution and dried over Na₂SO₄. Concentration in vacuo gave (4R)-4-benzyl-3-({(7R,8R)-7-[(benzyloxy)methyl]-1,4-dioxaspiro[4.5]dec-8-yl}carbonyl)-1,3-oxazolidin-2-one as a thick, tan colored syrup. ¹H NMR (500 MHz, d₆-acetone) δ 7.36-7.22 (10H, m), 4.48 (1H, m), 4.42 (2H, s), 4.11 (1H, dd, J= 3.1, 8.9 Hz), 3.97 (4H, m), 3.94-3.90 (1H, t, J= 9.0 Hz), 3.67 (1H, m), 3.44-3.38 (2H, m), 3.09 (1H, dd, J= 3.3, 13.5 Hz), 2.92 (1H, dd, J= 8.3, 13.5 Hz), 2.52 (1H, m), 1.97 (1H, m), 1.86-1.76 (3H, m), 1.57-1.50 (1H, m), 1.44 (1H, t, J= 12.8 Hz).

A solution of n-BuLi (2.4 M in hexanes, 75 mL) was added slowly to a solution of benzyl mercaptan (25 mL, 210 mmol) in THF (250 mL) at 0° C. The resulting pale-yellow solution was stirred at 0° C. for 15 min prior to the introduction of (4R)-benzyl-3-({(7R,8R)-7-[(benzyloxy)methyl]-1,4-dioxaspiro[4.5]dec-8-yl}carbonyl)-1,3-oxazolidin-2-one (64.2 g, 138 mmol) as a solution in THF (250 mL). After 30 min, a solution of LiAlH₄ (1.0 M in THF, 150 mL) was slowly added to the reaction mixture with continued stirring at 0° C. for 30 min. Ice water (15 mL) was then slowly added to destroy excess hydride followed by 6M HCl (110 mL) to pH 4. The mixture was extracted with two portions of ethyl acetate and the combined organics were washed with saturated aqueous NaCl and dried over Na₂SO₄. Concentration in vacuo and flash chromatography of the residue on silica gel eluting with 20/80 acetone/benzene afforded {(7R,8R)-7-[(benzyloxy)methyl]-1,4-dioxaspiro[4.5]dec-8-yl}methanol as a faint-yellow, thick syrup. ¹H NMR (500 MHz, d₆-acetone) δ 7.36 (4H, m), 7.29 (1H, m), 4.50 (2H, q, J=9.6 Hz), 3.90 (4H, s), 3.61 (1H, m), 3.52-3.42 (3H, m), 3.43 (1H, t, J= 5.5 Hz), 1.88-1.72 (4H, m), 1.55-1.41 (4H, m).

A solution composed of {(7R,8R)-7-[(benzyloxy)methyl]-1,4-dioxaspiro[4.5]dec-8-yl}methanol (33.6 g, 115 mmol) in a mixture of acetic acid (220 mL) and water (80 mL) was heated at 85° C. for 2 h. The solvents were removed by rotary evaporation under reduced pressure and the residue was partitioned between water and ethyl acetate. The aqueous phase was extracted with an additional portion of ethyl acetate and the combined organics were washed with saturated aqueous NaHCO$_3$ and NaCl solutions, and dried over a mixture of Na$_2$SO$_4$ and MgSO$_4$. Concentration in vacuo afforded a yellow syrup that was taken up in methanol (250 mL) and treated with K$_2$CO$_3$ (20 g, 150 mmol) with stirring at rt for 30 min. The methanol was then evaporated and the residue was taken up in ethyl acetate and washed with water, saturated aqueous NaCl solution, and dried a mixture of Na$_2$SO$_4$ and MgSO$_4$. Concentration in vacuo provided (3R,4R)-3-[(benzyloxy)methyl]-4-(hydroxymethyl)cyclohexanone as a thick, yellow syrup. $^1$H NMR (500 MHz, d$_6$-acetone) δ 7.36 (4H, m), 7.30 (1H, m), 4.56-4.50 (2H, m), 3.70 (1H, m), 3.66-3.60 (2H, m), 3.56 (1H, dd, J= 5.4, 9.3 Hz), 3.54-3.48 (1H, dd, J= 4.0, 9.3 Hz), 2.44-2.26 (4H, m), 2.13-2.07 (2H, m), 1.91 (1H, m), 1.67 (1H, m).

Hydrazine hydrate (110 mL. 2.3 mol) added to a suspension of activated 4A molecular sieve powder (110 g) in methanol (350 mL) with stirring at rt for 15 min. A solution of (3R,4R)-3-[(benzyloxy)methyl]-4-(hydroxymethyl)cyclohexanone (27.7 g, 112 mmol) in methanol (300 mL) was then added and the mixture was stirred at rt for 3 h. The sieves were removed by filtration and washed well with methanol. The methanol and excess hydrazine were evaporated by rotary evaporation under high vacuum with heating at 50° C. to remove the last traces of hydrazine. Meanwhile, a solution of CuCl$_2$ (106.6 g, 795 mmol) in methanol (370 mL) was treated with triethylamine (55 mL. 400 mmol) with stirring at rt for 15 min prior to cooling to 0° C. A solution of the crude hydrazone in methanol (300 mL) and then added dropwise over 35 min followed by slow warming to 10° C. over 4 h. The methanol was evaporated and the residue was partitioned between ethyl acetate and water and concentrated NH$_4$OH was added until all the solids dissolved. The layers were shaken and separated, and the aqueous phase was extracted with additional ethyl acetate. The combined organics were washed with concentrated aqueous NH$_4$OH, saturated NH$_4$Cl and NaCl aqueous solutions followed by drying over a mixture of Na$_2$SO$_4$ and MgSO$_4$. Concentration in vacuo and flash chromatography of the residue on silica gel eluting with 2/3 ethyl acetate/hexanes provided {(1R,2R)-2-[(benzyloxy)methyl]-4,4-dichlorocyclohexyl}methanol as a faint-yellow syrup. $^1$H NMR (500 MHz, d$_6$-acetone) δ 7.37 (4H, m), 7.31 (1H, m), 4.51 (2H, q, J= 12.2 Hz), 3.65-3.51 (5H, m), 2.66 (1H, dt, J= 3.9, 14.3 Hz), 2.54 (1H, dq, J= 3.3, 13.8 Hz), 2.29-2.19 (2H, m), 1.86 (1H, m), 1.75 (1H, m), 1.56 (1H, m). This material was converted to the title compound (colorless powder) according to the procedure used to prepare example 1 from {(1R,2R)-2-[(benzyloxy)methyl]-4,4-difluorocyclohexyl}methanol. $^1$H NMR (500 MHz, acetone d$_6$) δ 8.03 (1H, s), 8.01 (1H, overlapped br s), 7.98 (2H, d, J= 8.4 Hz), 7.80 (2H, d, J= 8.4 Hz), 5.06 (2H, q, J= 8.8 Hz), 3.43 (1H, m,), 3.29 (1H, dt, J= 3.3, 11.7 Hz), 3.19 (3H, s), 2.71 (1H, m), 2.58-2.68 (3H, m), 2.00-1.94 (2H, m), 1.43-1.31 (2H, m), 1.10 (1H, m), 0.86 (1H, m). MS: (+ESI) 563.1 [M+H]$^+$.

EXAMPLE 3

(1R,2R)-N-(1-cyanocyclopropyl)-5,5-difluoro-2-[4-[4-(methylsulfonyl)phenyl]-1-methyl-1H-pyrazol-3-yl]cyclohexanecarboxamide

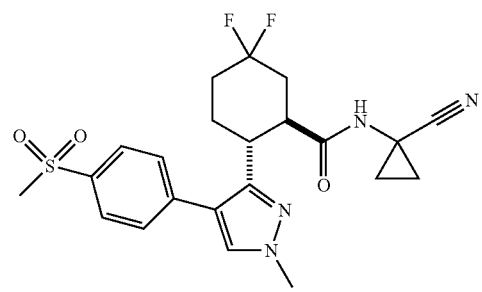

A solution of N-(cyanomethyl)-5,5-difluoro-2-{1-methyl-3-[4-(methylthio)phenyl]-1H-pyrazol-4-yl}cyclohexanecarboxamide (see example 4 in WO 2005/000800) (795 mg, 1.84 mmol) in CH$_2$Cl$_2$ (10 mL) was treated at 0° C. with purified m-CPBA (760 mg, 4.40 mmol) with stirring at this temperature for 30 min. Dimethyl sulphide was added to quench the excess m-CPBA and the mixture was partitioned between ethyl acetate and saturated aqueous sodium bicarbonate solution. The organic phase was dried (Na$_2$SO$_4$) and concentrated and the residue was purified by flash chromatography on silica to give to title compound as a colorless powder. $^1$H NMR (500 MHz, acetone d$_6$): δ 7.92 (2H, d, J=8.5 Hz), 7.80 (1H, s), 7.77 (1H, s), 7.72 (2H, d, J= 8.5 Hz), 3.88 (3H, s), 3.28 (1H, m), 3.14 (3H, s), 3.03 (1H, m), 2.20 (1H, m), 2.10-1.90 (4H, m), 1.80 (1H, m), 1.35 (1H, m), 1.30 (1H, m), 1.00 (1H, m), 0.77 (1H, m). MS: (+ESI) 463.1 [M+H]$^+$.

EXAMPLE 4

(1R,2R)-N-(1-cyanocyclopropyl)-5,5-dichloro-2-[4-[4-(methylsulfonyl)phenyl]-1-methyl-1H-pyrazol-3-yl]cyclohexanecarboxamide

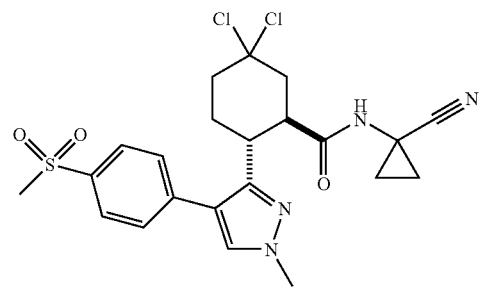

Prepared as a colorless powder according to the procedure for example 3 with substitution of hydrazine/CuCl$_2$/Et$_3$N (see Takeda, T.; Sasaki, R.; Yamauchi, S.; Fujiwara, T. *Tetrahedron* 1997, 53, 557) for the reaction with DAST. $^1$H NMR (500 MHz, acetone d$_6$): δ 7.92 (2H, d, J= 8.5 Hz), 7.87 (1H, s), 7.80 (1H, s), 7.71 (2H, d, J= 8.5 Hz), 3.88 (3H, s), 3.33 (1H, m), 3.20 (1H, m), 3.13 (3H, s), 2.67 (1H, m), 2.55-2.40 (3H, m), 1.95-1.90 (2H, m), 1.38 (1H, m), 1.32 (1H, m), 1.03 (1H, m), 0.80 (1H, m). MS (+ESI): 495.0 [M+H]$^+$.

EXAMPLE 5

(1R,2R)-N-(1-cyanocyclopropyl)-5,5-difluoro-2-[4-[4-(methylsulfonyl)phenyl]-1H-pyrazol-3-yl]cyclohexanecarboxamide

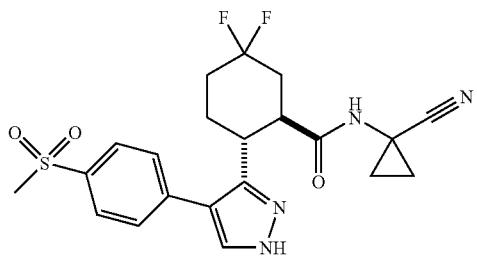

Demethylation of the pyrazole in 5,5-difluoro-2-{1-methyl-4-[4-(methylthio)phenyl]-1H-pyrazol-3-yl}cyclohexanecarboxylic acid (see example 4 in WO 2005/000800) according to the procedure of Butler and Dewald (see Butler, D. E.; Dewald, H. A; *J. Org. Chem.* 1975, 40, 1353) afforded 5,5-difluoro-2-{4-[4-(methylthio)phenyl]-1H-pyrazol-3-yl}cyclohexanecarboxylic acid. This compound was converted to the title compound by coupling with 1-aminocyclopropanecarbonitrile and oxidation with m-CBPA according to the standard procedures stated in the previous examples. $^1$H NMR (400 MHz, acetone d$_6$): δ 12.2 (1H, br s), 7.97 (2H, m), 7.92 (1H, br s), 7.78 (2H, m), 7.77 (1H, s), 3.38 (1H, br m), 3.18 (3H, s), 3.10 (1H, m), 2.22 (2H, m), 2.10 (2H, m), 2.00 (2H, m), 1.35 (2H, m), 0.98 (1H, m), 0.74 (1H, m). MS (+ESI): 449 [M+H]$^+$ Pharmaceutical Composition As a specific embodiment of this invention, 100 mg of (1R,2R)-5,5-dichloro-N-(1-cyanocyclopropyl)-2-[4-[4-(methylsulfonyl)phenyl]-1-(2,2,2-trifluoroethyl)-1H-pyrazol-3-yl]cyclohexanecarboxamide, is formulated with sufficient finely divided lactose to provide a total amount of 580 to 590 mg to fill a size 0, hard-gelatin capsule.

The compounds disclosed in the present application exhibited activity in the following assays. In addition, the compounds disclosed in the present application have an enhanced pharmacological profile relative to previously disclosed compounds.

ASSAYS

Cathepsin K Assay

Serial dilutions (1/3) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; DTT, 2.5 mM and 10% DMSO) and 25 of human cathepsin K (0.4 nM) in assay buffer solution. The assay solutions were mixed for 5-10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin L Assay

Serial dilutions (1/3) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; DTT, 2.5 mM and 10% DMSO) and 25 μL of human cathepsin L (0.5 nM) in assay buffer solution. The assay solutions were mixed for 5-10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin B Assay

Serial dilutions (1/3) from 500 μM down to 0.0085 μM of test compounds were prepared in dimethyl sulfoxide (DMSO). Then 2 mL of DMSO from each dilution were added to 50 μL of assay buffer (MES, 50 mM (pH 5.5); EDTA, 2.5 mM; DTT, 2.5 mM and 10% DMSO) and 25 μL of human cathepsin B (4.0 nM) in assay buffer solution. The assay solutions were mixed for 5-10 seconds on a shaker plate and incubated for 15 minutes at room temperature. Z-Leu-Arg-AMC (8 μM) in 25 mL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin S Assay

Serial dilutions (1/3) from 500 μM down to 0.0085 μM of test compounds were prepared in dimethyl sulfoxide (DMSO). Then 2 mL of DMSO from each dilution were added to 50 μL of assay buffer (MES, 50 mM (pH 5.5); EDTA, 2.5 mM; DTT, 2.5 mM and 10% DMSO) and 25 μL of human cathepsin S (20 nM) in assay buffer solution. The assay solutions were mixed for 5-10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Pharmacokinetics in Rats

Per Os (PO) Pharmacokinetics in Rats

Procedure:

The animals are housed, fed and cared for according to the Guidelines of the Canadian Council on Animal Care.

Male Sprague Dawley rats (250-400 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 0.5 mL of blood is collected into a heparinized vacutainer tube.

Compounds are prepared as required, in a standard dosing volume of 10 mL/kg, and administered orally by passing a 16 gauge, 3" gavaging needle into the esophagus.

Subsequent blood collections are taken in the same manner as the zero blood sample except that there is no need to nick the tail again. The tail is cleaned with a piece of gauze and milked/stroked as described above into the appropriately labeled tubes.

Immediately after sampling, blood is centrifuged, separated, the plasma put into clearly marked vials and stored in a freezer until analyzed.

Typical time points for determination of rat blood levels after PO dosing are:

0, 15 min, 30 min, 1 h, 2 h, 4 h, 6 h, 8 h, 24 h

After the 4 hr time point bleed, food is provided to the rats ad libitum. Water is provided at all times during the study.

Vehicles:

The following vehicles (with corresponding dose volumes) may be used in PO rat blood level determinations:

| | |
|---|---|
| PEG 200/300/400 (0-60% in water): | equal or less than 10 mL/kg |
| Methocel (0.5%-1.0% in water): | equal or less than 10 mL/kg |
| Tween 80 (1-10% in water): | equal or less than 10 mL/kg |

Compounds for PO blood levels can be in suspension form. For better homogeneity, the suspension can be placed in a sonicator for approximately 5 minutes.

For analysis, aliquots are diluted with 1.2 to 1.5 volumes of acetonitrile optionally containing an internal standard and centrifuged to remove protein precipitate. The supernatant is injected directly onto a C-18 HPLC column with mass spectrometry (MS) or ultra-violet absorbance (UV) or fluorescence (Fluo) detection. Quantization is done relative to a standard curve prepared using clean blood samples spiked with a known quantities of drug in acetonitrile optionally containing an internal standard. Additional acetonitrile optionally containing internal standard is added to amount 1.2 to 1.5 volumes of the initial blood amount to correspond to what was done in the case of the samples. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

and $$AUC = (C1+C2)*(T2-T1)/2$$

where C is the measured concentration by MS or UV or Fluo at a given time T

Intravenous Pharmacokinetics in Rats

Procedure:

The animals are housed, fed and cared for according to the Guidelines of the Canadian Council on Animal Care.

Male Sprague Dawley (325-375 g) non-fasted rats are used in theses studies.

The compound is prepared as required, in a standard dosing volume of 1 mL/kg.

Dosing of the conscious rats for intravenous administration is done via the jugular vein using a 25 gauge needle. This constitutes the zero time point.

The 5 min bleed is taken by nicking a piece (1-2 mm) off the tip of the tail. The tail is then stroked with a firm but gentle motion from the top of the tail to the bottom to milk the blood out of the tail. Approximately 0.5 mL of blood is collected into a heparinized collection vial. Subsequent bleeds are taken in the same fashion, except that there is no need to nick the tail again. The tail is cleaned with a piece of gauze and bled, as described above, into the appropriate labeled tubes.

Typical time points for determination of rat blood levels after I.V. dosing are either:

0, 5 min, 15 min, 30 min, 1 h, 2 h, 4 h, 6 h or 0, 5 min, 30 min, 1 h, 2 h, 4 h, 6 h, 8 h, 24 h Vehicles:

The following vehicles may be used in IV rat blood level determinations:

| | |
|---|---|
| Dextrose: | 1 mL/kg |
| Moleculosol 25%: | 1 mL/kg |
| DMSO (dimethylsulfoxide): | Restricted 10% of the dose volume up to 0.1 mL per kilogram of animal |
| PEG 200: | Not more than 80% mixed with 20% sterile water - 1 mL/kg |

With Dextrose, either sodium bicarbonate can be added if the solution is cloudy.

For analysis, aliquots are diluted with 1.2 to 1.5 volumes of acetonitrile optionally containing an internal standard and centrifuged to remove protein precipitate. The supernatant is injected directly onto a C-18 HPLC column with mass spectrometry (MS) or ultra-violet absorbance (UV) or fluorescence (Fluo) detection. Quantization is done relative to a standard curve prepared using clean blood samples spiked with a known quantities of drug in acetonitrile optionally containing an internal standard. Additional acetonitrile optionally containing internal standard is added to amount 1.2 to 1.5 volumes of the initial blood amount to correspond to what was done in the case of the samples. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

and $$AUC = (C1+C2)*(T2-T1)/2$$

where C is the measured concentration by MS or UV or Fluo at a given time T.

Hepatocyte Incubations

For rat hepatocyte incubations, $1\times10^6$ cells diluted in 0.5 mL of Krebs-Henseleit buffer were first prepared at 37° C. for 20 min under 95%:5% $O_2:CO_2$ (BOC gases: Montreal, Canada) in a 48-well plate, and the 5 μL of a 10 mM solution of compound dissolved in acetonitrile were added to each well to a final concentration of 50 μM. After 2 h of incubation at 37° C. under 95%:5% $O_2:CO_2$ atmosphere, one volume of acetonitrile was added in each well. A quenched incubation spiked with the parent compound and a blank were also prepared as controls. Once transferred, samples were centrifuged for 10 min at 14,000 rpm using an Eppendorf 5415C centrifuge (Hamburg, Germany) and the supernatant used for LC/UV/MS analysis.

What is claimed is:

1. A compound of the formula:

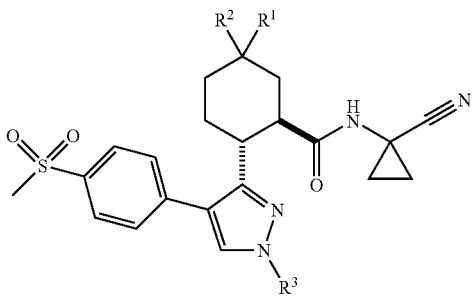

wherein $R^1$ is halo;
$R^2$ is halo;
$R^3$ is hydrogen, $C_{1-6}$ alkyl, $C_{1-6}$ haloalkyl, $C_{3-6}$ cycloalkyl, aryl or heteroaryl;
or a pharmaceutically acceptable salt, stereoisomer or N-oxide derivative thereof.

2. The compound of claim 1 wherein $R^1$ is fluoro or chloro; or a pharmaceutically acceptable salt, stereoisomer or N-oxide derivative thereof.

3. The compound of claim 2 wherein $R^2$ is fluoro or chloro; or a pharmaceutically acceptable salt, stereoisomer or N-oxide derivative thereof.

4. The compound of claim 3 wherein $R^3$ is hydrogen, $C_{1-6}$ alkyl or $C_{1-6}$ haloalkyl; or a pharmaceutically acceptable salt, stereoisomer or N-oxide derivative thereof.

5. The compound of claim 4 wherein $R^3$ is $C_{1-6}$ haloalkyl; or a pharmaceutically acceptable salt, stereoisomer or N-oxide derivative thereof.

6. The compound of claim 4 wherein $R^3$ is 2,2,2-trifluoroethyl; or a pharmaceutically acceptable salt, stereoisomer or N-oxide derivative thereof.

7. The compound of claim 1 which is:
- (1R,2R)-N-(1-cyanocyclopropyl)-5,5-difluoro-2-[4-[4-(methylsulfonyl)phenyl]-1H-pyrazol-3-yl]cyclohexanecarboxamide;
- (1R,2R)-N-(1-cyanocyclopropyl)-5,5-difluoro-2-[4-[4-(methylsulfonyl)phenyl]-1-methyl-1H-pyrazol-3-yl]cyclohexanecarboxamide;
- (1R,2R)-N-(1-cyanocyclopropyl)-5,5-dichloro-2-[4-[4-(methylsulfonyl)phenyl]-1-methyl-1H-pyrazol-3-yl]cyclohexanecarboxamide;
- (1R,2R)-N-(1-cyanocyclopropyl)-5,5-difluoro-2-[4-[4-(methylsulfonyl)phenyl]-1-(2,2,2-trifluoroethyl)-1H-pyrazol-3-yl]cyclohexanecarboxamide;
- (1R,2R)-N-(1-cyanocyclopropyl)-5,5-dichloro-2-[4-[4-(methylsulfonyl)phenyl]-1-(2,2,2-trifluoroethyl)-1H-pyrazol-3-yl]cyclohexanecarboxamide;

or a pharmaceutically acceptable salt, stereoisomer or N-oxide derivative thereof.

8. A pharmaceutical composition comprising a compound according to claim 1 and a pharmaceutically acceptable carrier.

9. A pharmaceutical composition comprising a compound of claim 1 and another agent selected from the group consisting of: an organic bisphosphonate, a selective estrogen receptor modulator, an estrogen receptor beta modulator, an androgen receptor modulator, an inhibitor of osteoclast proton ATPase, an inhibitor of HMG-CoA reductase, an integrin receptor antagonist, or an osteoblast anabolic agent, vitamin D, a synthetic Vitamin D analogue, a Nonsteroidal anti-inflammatory drug, a selective cyclooxygenase-2 inhibitor, an inhibitor of interleukin-1 beta, a LOX/COX inhibitor and the pharmaceutically acceptable salts and mixtures thereof.

* * * * *